(12) United States Patent
Wahidullah et al.

(10) Patent No.: US 7,138,368 B2
(45) Date of Patent: Nov. 21, 2006

(54) SESQUITERPENE OXIDES AS PERFUMING AND FLAVORING AGENTS

(75) Inventors: Solimabi Wahidullah, Goa (IN); Mangala Babu Govenkar, Mysore (IN); Shashikumar Keshav Paknikar, Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 226 days.

(21) Appl. No.: 10/400,189

(22) Filed: Mar. 26, 2003

(65) Prior Publication Data

US 2004/0192577 A1    Sep. 30, 2004

(51) Int. Cl.
*A61Q 13/00*    (2006.01)
(52) U.S. Cl. .............. 512/25; 512/8; 512/11; 512/22
(58) Field of Classification Search .......... 512/25, 512/22, 8, 11; 549/330, 331, 429, 456, 462
See application file for complete search history.

(56) References Cited

U.S. PATENT DOCUMENTS 4,311,860 A * 1/1982 Krasnobajew .......... 568/378

FOREIGN PATENT DOCUMENTS

| JP | 54084511 | * | 7/1979 |
| JP | 5484551 |   | 5/1997 |

* cited by examiner

*Primary Examiner*—Monique T. Cole
(74) *Attorney, Agent, or Firm*—Ohlandt, Greeley, Ruggiero & Perle, L.L.P.

(57) ABSTRACT

The present invention describes the process for the preparation of novel sesquiterpene oxide 3S,3aR,7aR,-6 isopropyl-1,1,3,3a-tetramethyl 1,3,3a,4,7,7a-hexahydro-isobenzofuran, of formula (I) by the reaction of elemol with per acid at a temperature range of 20 to 30° C. The invention also deals with the use of compound of formula (1) as a perfuming and flavoring agent

1

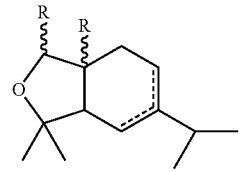

17 Claims, No Drawings

SESQUITERPENE OXIDES AS PERFUMING AND FLAVORING AGENTS

FILED OF THE INVENTION

The present inventions deals with a novel sesquiterpene oxide 3S,3aR,7aR,-6 isopropyl-1,1,3,3a-tetramethyl 1,3,3a,4,7,7a-hexahydro-isobenzofuran, of formula (I) and its process for preparation having odoriferous character. In addition, mixture of diastereoisomers of compound, of formula (1) in the ratio of 75:25 possesses multiodorant being a combination of rubarb, laurel, thyme and florex.

BACKGROUND OF PRIOR ART

The compounds as defined in formula 1, have been detected, among other reaction products, during the course of studies on peracid dehydration of the sesquiterpene elemol.

A Japanese patent JP 54084551 by Nagakura et al, published on 5th Jul., 1979 describes the use in perfumery, for cosmetics and flavor for food, of substances, specifically of an oily and multi-component oxidation product obtained by treating a mixture, consisting of alpha elemene and delta elemene, resulting from heat dehydration of beta elemol or an alpha elemene mixture separated from the dehydration product, with a peracid.

It is important to point out that this document of prior art neither specifies structure nor stereochemistry of any component of the mixture except giving the infrared and NMR spectra of the mixture. Without doubt, on the basis of the experimental conditions described in the abstract of the document, for the preparation of mixtures of diastereomers of elemenes oxides derived each from alpha and delta elemenes one may, theoretically expect the sesquiterpene alcohols, 2 and 3 as shown in the scheme-I.

Compound of formula (1) is neither prepared synthetically nor isolated from a natural product and reported the prior art. Its use as a perfuming or flavoring ingredient is also not known in the prior art.

During the synthesis of a reference compound, dehydration of elemol was carried out. The pleasant smelling novel sesquiterpene oxides, compounds of the present invention, were obtained as side products during the reaction.

OBJECT OF THE INVENTION

A main objective of the present invention provides a novel sesquiterpene oxide 3S,3aR,7aR, -6 isopropyl-1,1,3,3a-tetramethyl 1,3,3a,4,7,7a-hexahydro-isobenzofuran, of formula (I) and its process for preparation.

An object of the present invention provides compound of formula (1) having perfuming and flavoring property.

Still another object of the present invention is to provide a mixture of stereoisomers of compund of formula (1) having multuioderant being the combination of rhubarb, laurel, thyme and florex.

Yet another object of the present invention is to provide stereo isomers of compound of formula (1) having pronounced differences in their odoriferous properties. Still another object of the present invention is to utilise the compound of formula (1) in fine perfumery, colognes, hygiene products, hair care products, body deodorants, air fresheners and cosmetic preparations.

Still yet another object of the present invention, provides the use of a compound of formula (1) alone or in combination with other perfuming ingredients, solvents, or additives to obtain desired olfactory effect.

Yet another object of the present invention provides an incorporation of different proportions of compound of formula (1) into various products depending upon the nature of the products used and to obtain desired olfactory effect.

SUMMARY OF THE INVENTION

Accordingly, the present invention describes the process for the preparation of novel sesquiterpene oxide 3S,3aR,7aR,-6 isopropyl-1,1,3,3a-tetramethyl 1,3,3a,4,7,7a-hexahydro-isobenzofuran, of formula (I) by the reaction of elemol with per acid at a temperature range of 20 to 30° C. The invention also deals with the use of compound of formula (1) as a perfuming and flavoring agent.

BRIEF DESCRIPTION OF THE DRAWINGS

FORMULA 1 represents basic structure of novel sesquiterpene oxides

SCHEME-1 represents formation of elemene alcohols 2 & 3, probable products expected from reaction of elemenes, as per the reaction conditions given in JP 54084551.

DETAILED DESCRIPTION OF THE INVENTION

In accordance to the objects, the present invention provides a compound named 3S,3aR,7aR-6-isopropyl-1,1,3,3a-tetramethyl-1,3,3,9,4,7,7a-hexahydroisobenzofuran of formula (1).

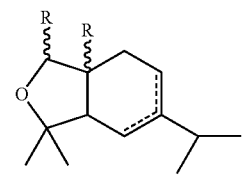

1

An embodiment of the present invention provides a compound having following characteristics:

Light yellow oil, $[\alpha]_D$-57.2(EtOH).

Infrared: 2964, 1377,1184, 950, 808, 777 $cm^{-1}$ $^1$H NMR (CDCl$_3$): δ 5.36 (1H, d, J=6.12 Hz); 3.55 (1H, q, J=7.2 Hz); 2.26 (1H, m); 1.24 (3H, s); 1.16 (3H, s); 0.77 (3H, s); 1.03 (6H, d, J=7.92 Hz); 1.13 (3H, d, J=7.2 Hz); 1.9, 1.72, 1.89, 1.75.

$^{13}$C NMR: 78.7; 81.2; 42.7; 37.7; 117.0; 143.4; 23.9; 54.3; 14.4; 12.6; 24.8; 30.6; 35.2; 21.4; 21.9 ppm.

MS: 222 (14), 207 (30), 178 (14), 163 (32), 149 (10), 135 (75), 93 (100), 79(18)

Still another embodiment of the present invention provides a compound having isobenzofuran ring responsible for olfactory characteristics.

Yet another embodiment of the present invention provides a compound used in fine perfumery, colognes, hygiene products, batch gels, hair care products, deodorants, air-freshener and cosmetic preparation.

Another embodiment of the present invention provides a compound as a single or as a mixture of isomers that can be used to impart fragrance to consumer products.

Still another embodiment of the present invention provides a process for the preparation of compound (1), the said process comprising steps of:
a) dissolving elemol in glacial acetic acid to obtain a solution,
b) adding perchloric acid to the step (a) solution at a temperature range of 20 to 30° C. to obtain a reaction mixture,
c) stirring the reaction mixture of step (b) at an ambient temperature for a period of 60 h to 80 h,
d) diluting with water the reaction mixture of step (d) extracting with the aqueous solution an organic solvent, separating the organic and the aqueous layer,
e) washing the organic layer of step (d) with aqueous sodium bicarbonate followed by water,
f) drying the washed organic layer over anhydrous sodium sulphate, filtering, and removing the solvent from the filtrate to obtain crude product, and
g) purifying the crude product of step (f) over silica gel column eluting with a mixture of organic solvent to obtain the compound of formula (1).

Still another embodiment of the present invention provides a process, wherein in step (b), the peracid used is selected from a group consisting of peracetic acid, perchloric acid or perbenzoic acid.

Yet another embodiment of the present invention provides a process, wherein in step (d) the organic solvent used is selected from diethylether, methylene, chloride, chloroform or ethylacetate.

Still another embodiment of the present invention provides a process, wherein in step (g) the mixture of organic solvent used is ethylacetate petroleum ether (4:96).

Yet another embodiment of the present invention provides a process having isobenzofuran ring responsible for olfactory characteristics.

Still another embodiment of the present invention provides a process wherein the compound is used in fine perfumery, colognes, hygiene products, batch gels, hair care products, deodorants, air freshness or cosmetic preparation. This compound can be used as an additive and when used in the applications, the products accepted to the users and it has not shown any adverse effect.

Yet another embodiment of the present invention provides a synergistic composition containing an effective amount of compound (I) or mixture of its isomers, the said composition being useful in perfuming the soaps, shower or bath gels, hygiene products, hair care products such as shampoos, body deodorants, air fresheners or cosmetic preparation.

Still another embodiment of the present invention provides a composition that can be used alone or in combination with other perfuming agents, solvents or additives.

Yet another embodiment of the present invention provides a composition, wherein the mixture of isomers of compound (I) in the ratio 75:25 is a multiodorant being a combination of rhubarb, laurel, thyme and florex.

The invention is illustrated with references to the examples, which should not be construed to limit the scope of the present invention.

EXAMPLE 1

Preparation of the Compounds of Formula 1

To a solution of elemol (3.5-gm) in glacial acetic acid (42 ml) was added perchloric acid (0.7 ml, 60%). The reaction mixture was allowed to stand at room temperature (25–27° C.) for 72 hours with continuous stirring, The reaction product was diluted with water and extracted with ether. The ethereal extract washed with sodium bicarbonate, then with water and dried over anhydrous sodium sulfate. Removal of the solvent gave a crude product containing, besides elemenes (major product of the reaction) all the stereoisomers of sesquiterpene oxide. The preferred compound is a major component of the stereoisomeric mixture.

EXAMPLE 2

Purification of the preferred compound, 3S,3aR,7aR-6 isopropyl-1,1,3,3a-tetramethyl 1,3,3a,4,7,7a, hexahydro isobenzofuran:

The crude product was flash column chromatographed over silica gel with ethyl acetate in petroleum ether (4:96) to yield the preferred compound. Rf of the compound in the same solvent system as the eluent is 0.6.Yield: 0.28 g.

Analytical Data:
Llight yellow oil, $[\alpha]_D$-57.2 (EtOH).
Infrared: 2964, 1377,1184, 950, 808, 777 cm$^{-1}$
$^1$H NMR (CDCl$_3$): δ 5.36 (1H, d, J=6.12 Hz); 3.55 (1H, q, J=7.2 Hz); 2.26 (1H, m); 1.24 (3H, s); 1.16 (3H, s); 0.77 (3H, s); 1.03 (6H, d, J=7.92 Hz); 1.13 (3H, d, J=7.2 Hz); 1.9, 1.72, 1.89, 1.75.
$^{13}$C NMR: 78.7; 81.2; 42.7; 37.7; 117.0; 143.4; 23.9; 54.3; 14.4; 12.6; 24.8; 30.6; 35.2; 21.4; 21.9 ppm.
MS: 222 (14), 207 (30), 178 (14), 163 (32), 149 (10), 135 (75), 93 (100), 79 (18)

ADVANTAGES OF THE PRESENT INVENTION

1. The molecule is novel with the novel application
2. It is multi-odorant with the tonalities of rhubarb, laurel, thyme and florex.
3. This compound can be used as an additive and when used in the applications, the products accepted to the users and it has not shown any adverse effect.

What is claimed is:

1. A compound 3(S), 3a(R), 7a(R)-6-isopropyl-1,1,3,3a-tetramethyl-1,3,3a,4,7,7a-hexahydroisobenzofuran of formula (1):

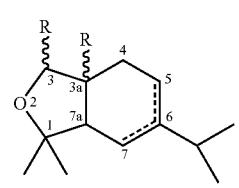

(1)

wherein (S) and (R) denote absolute configuration at the carbon at the specified position;
wherein R is methyl;
wherein the wavy lines represent the two possible positions of the R groups relative to the plane of the rings to which they are attached and include isomers wherein the R groups are either cis- or trans-;
wherein the dotted lines denote an unsaturated bond at a location selected from the group consisting of: between C5 and C6 and between C6 and C7.

2. A compound according to claim 1, which is an isomeric mixture and which exhibits pronounced olfactory characteristics.

3. A compound according to claim 1, further comprising ingredients suitable for use in fine perfumery, colognes, hygiene products, batch gels, hair care products, deodorants, air freshener or cosmetic preparation.

4. A compound according to claim 3, as a mixture of isomers that can be used to impart fragrance to consumer products.

5. A process for the preparation of compound 3(S), 3a(R), 7a(R)-6-isopropyl-1,1,3,3a-tetramethyl-1,3,3a,4,7,7a-hexahydroisobenzofuran of formula (1):

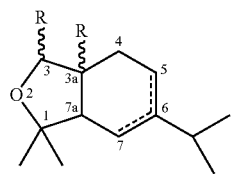

(1)

wherein (S) and (R) denote absolute configuration at the carbon at the specified position;
wherein the wavy lines represent the two possible positions of the R groups relative to the plane of the rings to which they are attached and include isomers wherein the R groups are either cis- or trans-;
wherein R is methyl; and
wherein the dotted lines denote an unsaturated bond at a location selected from the group consisting of: between C5 and C6 and between and C6 and 7;
said process comprising steps of:
a) dissolving elemol in glacial acetic acid to obtain a solution;
b) adding perchlorid acid to the solution in step (a) at a temperature in the range of 20° to 30° C. to obtain a reaction mixture;
c) stirring the reaction mixture of step (b) at ambient temperature for a period of 60 hrs to 80 hrs;
d) diluting the reaction mixture of step (d) with water and extracting with an organic solvent;
e) washing the organic layer of step (d) with aqueous sodium bicarbonate followed by water;
f) drying the washed organic layer over anhydrous sodium sulphate, filtering, and removing the solvent from the filtrate to obtain a crude product; and
g) purifying the crude product of step (f) over silica gel column by eluting with a mixture of organic solvent to obtain the compound of formula (1).

6. A process of claim 5, wherein the per acid used in step (b) is selected from a group consisting of: peracetic acid perchloric acid and perbenzoic acid.

7. A process according to claim 5, wherein the organic solvent used in step (d) is selected from the group consisting of: diethyl ether, methylene chloride, chloroform and ethyl acetate.

8. A process according to claim 5, wherein the mixture of organic solvent used in step (g) is ethyl acetate/petroleum ether (4:96).

9. A process according to claim 5, wherein the compound obtained in step (g) is an isomeric mixture that exhibits pronounced olfactory characteristics.

10. A process according to claim 5, wherein the compound obtained further comprises ingredients suitable for use in fine perfumery, colognes, hygiene products, batch gels, hair care products, deodorants, air freshness or cosmetic preparations.

11. A composition containing an effective amount of compound (I) or mixture of its isomers and ingredients suitable for use in perfuming the soaps, shower or bath gels, hygiene products, hair care products, shampoos, body deodorants, air fresheners or cosmetic preparation.

12. A composition according to claim 11, comprising an effective amount of compound (I) or mixture of its isomers in combination with other perfuming agents, solvents and/or additives.

13. A composition according to claim 11, wherein the mixture of isomers of compound (I) is in combination with rhubarb, laurel, thyme and florex in the ratio 75:25.

14. A compound 3(S), 3a(R), 7a(R)-6-isopropyl-1,1,3,3a-tetramethyl-1,3,3a,4,7,7a-hexahydroisobenzofuran of formula (1):

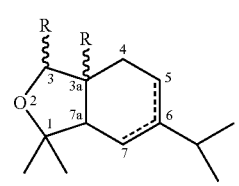

(1)

wherein (S) and (R) denote absolute configuration at the carbon at the specified position;
wherein R is methyl;
wherein the wavy lines represent the two possible positions of the R groups relative to the plane of the rings to which they are attached and include isomers wherein the R groups are either cis- or trans-;
wherein the dotted lines denote an unsaturated bond at a location
selected from the group consisting of: between C5 and C6 and between and C6 and C7;
said compound having a composition that exhibits the following characteristics:
Llight yellow oil, $[\alpha]_D$-57.2 ( EtOH);
Infrared: 2964, 1377,1184,950,808, 777 cm$^{-1}$;
$^1$H NMR (CDCl$^3$): δ 5.36 (1H, d, J=6.12 Hz); 3.55 (1H,q,J=7.2 Hz); 2.26 (1H, m); 1.24 (3H, s); 1.16 (3H, s); 0.77 (3H, s); 1.03 (6H, d, J=7.92 Hz); 1.13 (3H, d, J=7.2 Hz); 1.9, 1.72, 1.89, 1.75;
$^{13}$C NMR: 78.7; 81.2; 42.7; 37.7; 117.0; 143.4; 23.9; 54.3; 14.4; 12.6; 24.8; 30.6; 35.2; 21.4; 21.9 ppm; and
MS: 222 (14), 207 (30), 178 (14), 163 (32), 149 (10), 135 (75), 93 (100), 79 (18).

15. A compound according to claim 14, which is an isomeric mixture and which exhibits pronounced olfactory characteristics.

16. A compound according to claim 14, further comprising ingredients suitable for use in fine perfumery, colognes, hygiene products, batch gels, hair care products, deodorants, air freshener or cosmetic preparation.

17. A compound according to claim 16, as a mixture of isomers that can be used to impart fragrance to consumer products.

* * * * *